(12) United States Patent
Chiu et al.

(10) Patent No.: US 7,034,207 B2
(45) Date of Patent: Apr. 25, 2006

(54) **PAPAYA (*CARICA PAPAYA* L) VARIETY**

(75) Inventors: Chan-Tai Chiu, Ping Tong Hsien (TW); Chi-Hsiung Shiau, Taichung (TW); Tian-Shyong Ko, Taichung (TW); Loong-Sheng Chang, Taipei (TW)

(73) Assignee: Taiwan Seed Improvement and Propagation Station, Council of Agriculture, Executive Yuan, Taichung (TW)

( * ) Notice: Subject to any disclaimer, the term of this patent is extended or adjusted under 35 U.S.C. 154(b) by 20 days.

(21) Appl. No.: 10/926,668

(22) Filed: Aug. 26, 2004

(65) Prior Publication Data

US 2006/0053506 A1    Mar. 9, 2006

(51) Int. Cl.
*A01H 1/00*    (2006.01)
*A01H 5/00*    (2006.01)
*C12N 5/00*    (2006.01)
*C12N 5/02*    (2006.01)

(52) U.S. Cl. .................. 800/298; 800/260; 435/410; 435/430

(58) Field of Classification Search ............... 800/260, 800/298, 309; 435/410, 430
See application file for complete search history.

(56) References Cited

U.S. PATENT DOCUMENTS

PP12,481 P2 * 3/2002 Fitch .................. Plt./156

OTHER PUBLICATIONS

Storey, W.B. "*Carica papaya*", pp. 147-154, *CRC Handbook of Flowering*, vol. II, 1985.

Storey, W.B. "Papaya: *Carica papaya* (Caricaceae)", pp. 21-24, *Evolution of Crop Plants*, Simmonds, N.W., Editor, Longman, Scientific & Technical, 1984.

Giacometti, D.C. "Papaya Breeding", *Acta Horticulture* (1987), 196: 53-60.

Manshardt, Richard M. "Papaya", Chapter 21, pp. 489-511. *Biotechnology in Agriculture*, Hammerschlag, F.A. and R.E. Litz, editors. Wallington, Oxford, UK, 1992.

Nakasone, Henry. Y. "Papaya", pp. 277-301, *CRC Handbook of Fruit Set and Development*, vol. II. Monselise, S.P., editor. CRC Press: Boca Raton, Florida, 1986.

Storey, W.B. "Genetics of the Papaya", *The Journal of Heredity* (1953), 44:70-78.

Parasnis, A.S. et al, "Microsatellite $(GATA)_n$ reveals sex-specific differences in Papaya", *Theor Appl Genet* (1999), 99: 1047-1052.

Storey, William B. "Papaya: *Carica papaya* L.", pp. 389-407, *Outlines of perennial crop breeding in tropics*, Ferwerda, F.P. and F. Wit, editors. Wageringen, The Netherlands, 1969.

Parasnis, A.S. et al. "A highly reliable sex diagnostic PCR assay for mass screening of papaya seedlings", *Molecular Breeding* (2000), 6: 337-344.

* cited by examiner

*Primary Examiner*—David H. Kruse
*Assistant Examiner*—Keith O. Robinson
(74) *Attorney, Agent, or Firm*—Ladas & Parry LLP

(57) ABSTRACT

The present invention provides an all hermaphroditic papaya variety and their seeds, pollans, tissue cultures, parts of plant and the method for producing them.

17 Claims, No Drawings

PAPAYA (*CARICA PAPAYA* L) VARIETY

FIELD OF THE INVENTION

The invention relates to a new hermaphroditic papaya variety which produces all hermaphroditic progenies.

BACKGROUND OF THE INVENTION

Papaya (*Carica papaya* L.) is an important tropical fruit crop with a yielding potential of approximately 45 tons/hectare, which is normally consumed fresh and is valued as a health food because it is rich in vitamins C and A. Papaya is widely grown in Brazil, Australia, South Africa, South-East Asia, Hawaii, India and other tropical areas. Papaya is a polygamous species, and sex inheritance is controlled by a single locus with multiple alleles. There are three sex forms of papaya trees, i.e. hermaphrodite or bisexual, pistillate or female, and staminate or male. The sex types of papaya may not be identified according to the phenotype of the juvenile plant or other chemical or biochemical methods. The male, female and hermaphroditic flowers of papaya are distributed on separate papaya plants and sex types are revealed only after flowering. Methods to identify sex type at juvenile stage have been studied (Bojappa and Singh 1974, Choudhri et al. 1957, Parasnis et al. 1999, 2000; Singh et al. 1977, Sondur et al. 1996, Somsri et al. 1998). Storey proposed that the sex of papaya is determined by three homologous gene complexes on sex chromosome (W. B. Storey, J. Hered. 44, 70–78, 1953; and W. B. Storey, Crop Plants, 21–24. Wisley, N.Y.). The genes are so tightly linked that no crossing over occurs among them; thus the complexes are transmitted to offspring as if they are single gene alleles with pleiotrophic effects on phenotypic expression. The genotypes of the male, hermaphroditic and female plants are $M_1m$, $M_2m$, and $mm$, respectively. Genotypes with homozygous dominant alleles are lethal (W. B. Storey, J. Hered. 44, 70–78, 1953).

The hermaphroditic papaya, bearing perfect flowers and producing fruits shaped from long-cylindrical to ellipsoidal, is preferred by the markets in Hawaii, Japan, South-East Asia and Taiwan. In addition, the consumers and farmers prefer hermaphrodite papaya because it has small seed cavity and is easier to package. The cross between two hermaphroditic papayas will yield a ratio of 2:1 hermaphrodite to female papaya. Therefore, the papaya growers usually plant at least two seedlings in each hole in the field, and later remove the females at flowering, a practice that is time-consuming and wasteful. Therefore, there is a need to develop a technology of obtaining all hermaphrodite papaya.

SUMMARY OF THE INVENTION

The invention provides to seeds of papaya inbred line designated Taiwan Seed Station No. 7 (TSS No. 7), the papaya plant produced by growing the seed and the parts of the plant.

DETAILED DESCRIPTION OF THE INVENTION

The present invention provides an all hermaphroditic papaya variety and their seeds, pollans, tissue cultures, parts of plant and the method for producing them.

New Hermaphroditic Papaya Mutant

The invention provides an all hermaphroditic papaya variety, Taiwan Seed Station No. 7 (TSS No. 7), which is derived from the "Sunrise" papaya cultivar mutant. TSS No. 7 generates all hermaphroditic progenies and the trait can be transferred to other papaya cultivars. TSS No. 7 produces fruit weighing approximately 500 g and tastes like "Sunrise." TSS No. 7 contains two genes to control the sex expression, one being lethal mutant gene ($l_1$) tightly linked to m and another forming the dominant allele. The traits of TSS No. 7 are as follows:

1. Plant
   Plant gender: hermaphrodite trees
   Size: height larger than 150 cm, about 18 cm in diameter
   Nodes of first flower: 25
   Length betweens nodes: 2.9 cm in average
   Height at first harvest: less than 1 meter
   Average fruit numbers: average 47/plant
   Production (kg/year): less than 50 kg
      Maturity of fruit: 111 to 140 days
   Bark color: light grayed-brown
      Foliage density: 27.8 leaves in average at the apex
      Maturity: 113–140 from pollination to first harvest
2. Leaf
   Mature petiole color: green
   Mature Petiole length: 77.2 cm in average
   Mature Petiole diameter: 1.39 cm in average
   Leaf lamina length: 71.1 cm in average
   Leaf lamina width: 65.6 cm in average
   Form: shallowly lobed palmate
3. Flowers
   Hermaphrodite
   Color of inflorescence stalk: light green
   Flower number per node: 1–3
   Size: small
   Color: white-yellow
4. Fruit
   Form
   Form: pear-like shape
   Base attached to peduncle: flat
   Skin
   Color: Dark yellow-orange
   Texture: Average to gritty, medium firm to firm
   Thickness: medium
   Flesh
   Color: orange to dark red
   Flavor: strong
   Firmness: firm
   Fibers: exist
   Eating quality: exceptionally high
   Seed cavity at central position: star-shaped
   Seed cavity width at central position: 4.3 cm in average
   Fruit weight: average 500 g
   Fruit length: average 14.1 cm
   Fruit width: average 8.5 cm
   Brix: 13 degree
5. Seeds
   Color: brown black
   Shape: round or oval
   Surface: dark, opacity and slimy
   Average dry weight per 100 seeds: 0.94 g
   Average wet weight of seeds in a fruit: 29.1 g
6. Insect Resistance
   Red spider: High Susceptible
   White spider: Susceptible
   Scale: Susceptible Nematodes: Susceptible
Snail: Susceptible
7. Disease Resistance
Anthracnose: High Susceptible
*Phytophthora* fruit rot: High Susceptible
Powdery mildew: High Susceptible
Root rot: Susceptible
Seedling blight: High Susceptible
Stem-end rot: Susceptible
Virus Disease: Very High Susceptible
*Phytophthora* palmivora Butler: Susceptible
Melanose: Susceptible
Black rot: Susceptible Self-pollination of TSS No. 7 results in all progenies being hermaphroditic. A genetic study has indicated that two genes control the sex expression in the TSS No. 7, one being a lethal mutant gene ($l_1$), which is tightly linked to m, designated as $ml_1$, and the other is a variety of the dominant $M_2$ allele. According to Storey's model, homozygous genotypes ($M_2M_2$) would be lethal (W. B. Storey, J. Hered. 44, 70–78, 1953; and W. B. Storey, Crop Plants, 21–24. Wisley, N.Y.). The genotype of homozygous female, $ml_1ml_1$, is lethal because of the expression of the lethal gene. The hermaphroditic papaya containing female recessive lethal gene ($M_2$ $ml_1$) can live because it contains a single lethal gene ($l_1$) that cannot be expressed. The progenies of the inbrids or hybrids of the hermaphroditic papaya containing female recessive lethal gene have the genotypes: 1 $M_2M_2$: 2 $M_2$ $ml_1$: 1 $ml_1ml_1$. Since $M_2M_2$ and $ml_1ml_1$ are lethal, only hermaphroditic papaya remains. Therefore, TSS No. 7 has the genotype of $M_2$ $ml_1$ and is capable of producing all hermaphroditic papaya progenies.

Production of the New Hermaphroditic Papaya Variety

Seeds of self-pollinated hermaphroditic "Sunrise" are planted. It is found that the plants of a cultigen, designated as "SR*-1," are all hermaphroditic papaya. One of the progenies of "SR*-1," designated as "SR*-1-1," is selected and self-pollinated to evaluate the sex expression in the next generation. The progenies of "SR*-1-1" all expressed the hermaphroditic sex type, which is designated as "SR*-1-1-1." The new breeding all hermaphroditic papaya is designated as "TSS No. 7."

This invention includes seeds of "TSS No. 7" and the plants produced therefrom. The invention also includes plant cell tissue cultures from which "TSS No. 7" plants can be regenerated, or parts of plants, such as pollen, seeds, offshoot, cutting, grafting and the like.

EXAMPLE

Seeds of self-pollinated hermaphroditic "Sunrise" were collected and stored separately at 10° C., 50% relative humidity for 5 years before planting. Fifteen plants per selfed progeny were planted in 1.5×3.5-m rows in a net house in a field, and only one progeny gave all hermaphroditic progenies. One plant was randomly selected from the fifteen and self-pollinated to evaluate the sex expression in the next generation. Twenty seedlings all expressed the hermaphroditic sex type, and the Code SR*-1 was given to represent this hermaphroditic cultigen. One random plant out of the 20 plants of SR*-1 was chosen and selfed to obtain seeds of SR*-1-1, from which SR*-1-1-1 and SR*-1-1-1-1 were derived in the following generations by the same strategy. SR*-1-1-1 plants were grown at two locations for two seasons and SR*-1-1-1-1 plants were grown at one location for one season to evaluate their respective performances. The seedlings of SR*-1-1-1, "Sunrise" and "Thailand" were planted in September and December 1998 and those of SR*-1-1-1-1 were planted in a field in Pingtung in southern Taiwan. Also, some seedlings of SR*-1-1-1-1 were planted in a field in Kaoshu, a separate location in Southern Taiwan, in 1998. At least 100 plants for each papaya cultivar were planted and the sex types of the plants were recorded at flowering.

Four hybridizations were produced for genetic studies in December 1998: hermaphroditic "Thailand" as the female with hermaphroditic "Sunrise" as the male; hermaphroditic "Thailand" as the female with SR*-1-1-1-1 (three randomly selected SR*-1-1-1-1) as the male; female "Thailand" with hermaphroditic "Sunrise" as the male; and female "Thailand" with SR*-1-1-1-1 (another three randomly selected SR*-1-1-1-1) as the male. All combinations shared one common inbred parent, "Thailand", and their hybrids had the same genetic background, except for the mutation region between "Sunrise" and SR*-1-1-1-1. The hybrid seedlings were planted with two replications in 1.5×3.5-m rows in a field in November 1999. The sex types of the plants were recorded at flowering. 20 $F_1$ plants selected randomly from a hybrid located between the hermaphroditic "Thailand" and SR*-1-1-1-1 were selfed to obtain one $F_2$ generation, and $F_1$ plants selected randomly from a hybrid located between female "Thailand" and SR*-1-1-1-1 were selfed to obtain another $F_2$ generation. The seedlings of the $F_2$s were planted to evaluate the sex type segregation.

Self-pollination of hermaphroditic "Thailand" and "Sunrise" papaya produced a 2:1 ratio of hermaphroditic ($M_2m$) and female plants (mm), agreeing with Storey's model (Table 1). The sexual types of papaya progeny were all hermaphroditic from selfing of SR*-1-1-1 or SR*-1-1-1-1 regardless of the planting location, season or generation (Table 1). As shown in Table 1, SR*-1-1-1 and SR*-1-1-1-1 produced all the hermaphroditic progenies without any female plant, thus suggesting a second recessive lethal gene (I) linked to the m allele, which caused the death of the female papayas. The putative genetic model of these lethal female progenies of the SR* derivatives is mlml.

TABLE 1

| | | No. of progeny | | | | |
|---|---|---|---|---|---|---|
| Cultivars | Date planted | Herm. (♂) | Female (♀) | Expected ratio | $\chi^2$-value ratio | Proposed |
| Thailand ♂ | September 1998 | 168 | 80 | 2:1 | 0.085 n.s. | 2:1 |
| Sunrise ♂ | September 1998 | 79 | 41 | 2:1 | 0.009 n.s. | 2:1 |
| SR*-1-1-1[1] | April 1999 | 53 | 0 | 2:1 | 20.78† | 1:0 |

TABLE 1-continued

|  |  | No. of progeny | | | | |
| --- | --- | --- | --- | --- | --- | --- |
| Cultivars | Date planted | Herm. (♂) | Female (♀) | Expected ratio | $\chi^2$-value ratio | Proposed |
| SR*-1-1-1[2] | September 1998 | 104 | 0 | 2:1 | 49.04† | 1:0 |
| SR*-1-1-1[2] | December 1998 | 120 | 0 | 2:1 | 58.50† | 1:0 |
| SR*-1-1-1[2] | October 1999 | 130 | 0 | 2:1 | 62.76† | 1:0 |

[1]Progeny plants of SR* planted at a separate location.
[2]Progeny plants planted at the same location.
n.s.: not significant at P = 0.05; † significant at P = 0.01.

Table 2 summarizes the segregation of the hermaphroditic and female progenies from the crosses. "Tainung no. 2", the cross from the hermaphroditic parents "Thailand" and "Sunrise", gave a 2:1 ratio, and crosses between female maternal "Thailand" and hermaphroditic "Sunrise" and between female "Thailand" and SR* both gave a 1:1 ratio. All these ratios agreed with Storey's model. The cross between hermaphroditic "Thailand" and SR*-1-1-1-1 gave a 3:1 segregation ratio instead of 2:1, revealing the survival rate of the homozygous hermaphroditic genotype. To identify the survival of the hermaphroditic $F_1$ genotype with dominant alleles, 20 hermaphroditic $F_1$s from the cross between hermaphroditic "Thailand" and the SR*-1-1-1-1 mutant were randomly selected and self-pollinated to obtain $F_2$ segregates. There are two expected segregation ratios in Table 3, i.e. 2:1 and 1:0. However, F1 plants 6, 8, 9, 13 and 20 led to a ratio with 6–15% being female, significantly less than the expected 2:1. SR*-1-1-1-1 with hermaphroditic "Thailand" gave a segregation ratio of 3:1 instead of 2:1, which revealed the survival of the homozygous hermaphroditic genotype and suggested that the dominant allele derived from the SR*-1-1-1-1 papaya was different from the $M_2$ of the hermaphroditic "Sunrise". Therefore, the $M_@$ allele was designated to the hermaphroditic SR* instead of $M_2$ as in the hermaphroditic "Sunrise". As shown in Table 2, the genotype of SR* is $M_@ml$, and the hybrids between "Thailand" and SR* would thus be $M_2M_@$, $M_@m$, $M_2ml$ and $mml$, giving a 3:1 ratio of hermaphrodite to female papayas. The proportion of hermaphroditic plants in the cross "Thailand"× SR-1-1-1-1 is 75% instead of only 66.7% in the cross between "Thailand"×"Sunrise", known as "Tainung no. 2".

TABLE 3

| Parental combination | No. of $F_2$ plants[1] | | Expected ratio[1] | $Z^2$-values 2:1 | Putative genotypes of the selected $F_1$ plants |
| --- | --- | --- | --- | --- | --- |
| | Herm. (♂) | Female (♀) | | | |
| 'Thailand' (♂) x SR*-1-1-1-1 $F_1$ plant | | | | | |
| 1 | 63 | 27 | 2:1 | 0.313 n.s. | $M_@m$ |
| 2 | 102 | 57 | 2:1 | 0.347 n.s. | $M_@m$ |
| 3 | 26 | 14 | 2:1 | 0.003 n.s. | $M_@m$ |
| 4 | 104 | 38 | 2:1 | 2.473 n.s. | $M_@m$ |
| 7 | 22 | 10 | 2:1 | 0.003 n.s | $M_@m$ |
| 10 | 58 | 25 | 2:1 | 0.255 n.s | $M_@m$ |
| 11 | 22 | 13 | 2:1 | 0.089 n.s | $M_@m$ |
| 12 | 22 | 10 | 2:1 | 0.003 n.s | $M_@m$ |
| 15 | 110 | 62 | 2:1 | 0.454 n.s | $M_@m$ |
| 16 | 27 | 13 | 2:1 | 0.003 n.s | $M_@m$ |
| 17 | 17 | 10 | 2:1 | 0.005 n.s | $M_@m$ |
| 18 | 29 | 16 | 2:1 | 0.025 n.s | $M_@m$ |
| 19 | 119 | 58 | 2:1 | 0.006 n.s | $M_@m$ |
| 5 | 38 | 0 | 1:0 | 17.53† | $M_2ml$ or $M_@M_2$ |
| 14 | 43 | 0 | 1:0 | 20.03† | $M_2ml$ or $M_@M_2$ |
| 6 | 109 | 7 | ? | 37.69† | $M_2ml$ or $M_@M_2$ |
| 8 | 111 | 14 | ? | 26.57† | $M_2ml$ or $M_@M_2$ |
| 9 | 133 | 14 | ? | 36.44† | $M_2ml$ or $M_@M_2$ |
| 13 | 159 | 27 | ? | 28.80† | $M_2ml$ or $M_@M_2$ |
| 20 | 102 | 10 | ? | 28.93† | $M_2ml$ or $M_@M_2$ |

TABLE 2

| Parental plants | No. of segregating plants | | Proposed ratio | $\chi^2$-values | Genotypes of hybrid plants | |
| --- | --- | --- | --- | --- | --- | --- |
| | Herm (♂) | > Female (♀) | | | Herm. (♂) | Female (♀) |
| Thailand ♂ × sunrise | 62 | 30 | 2:1 | 0.001 n.s. | $M_2m$ | mm |
| Thailand ♀ × sunrise | 47 | 50 | 1:1 | 0.041 n.s. | $M_2m$ | mm |
| Thailand ♀ × SR*-1-1-1-1 | 88 | 95 | 1:1 | 0.199 n.s. | $M_@M$ | mml |
| Thailand ♂ × SR*-1-1-1-1 | 119 | 41 | 3:1 | 0.008 n.s. | $M_@m$ $M_2ml$ | mml |

$\chi^2$-square tests were calculated using Yates correction formula.
n.s.: not significant at P = 0.05.

TABLE 3-continued

| Parental combination | No. of F$_2$ plants[1] Herm. (♂) | No. of F$_2$ plants[1] Female (♀) | Expected ratio[1] | Z$^2$-values 2:1 | Putative genotypes of the selected F$_1$ plants |
|---|---|---|---|---|---|
| | | 'Thailand' ♀ SR*-1-1-1-1 F$_1$ plant | | | |
| 1 | 77 | 45 | 2:1 | 0.542 n.s | M@m |
| 2 | 87 | 44 | 2:1 | 0.001 n.s | M@m |

X$^2$-square tests were calculated using Yates correction formula.
[1]Segregation ratio of hermaphrodite to female sex types according to Storey's model.
M$_@$M$_@$ homozygous dominant is lethal.
M$_2$M$_2$ homozygous dominant is lethal.
mlml homozygous recessive is lethal.
n.s.: not significant at P = 0.05;
†significant at P = 0.01.

The three putative genotypes derived from the F$_1$ plants (hermaphroditic "Thailand"×SR-1-1-1-1) were M$_@$M$_@$, M$_@$m, and mm for M$_@$m, and M$_@$M$_@$, M$_@$M$_2$, and M$_2$M$_2$, for M$_@$M$_2$, and M$_2$M$_2$, M$_2$ml, and mlml for M$_2$ ml. However, two different hermaphroditic to female segregation ratios, 2:1 and 1:0, were obtained, indicating that the homozygous dominant genotype, M$_@$M$_@$, did not survive (Table 3). Therefore, M$_@$M$_@$ was as lethal as M$_2$M$_2$ and mlml; and thus, self-pollination of M$_@$m resulted in a 2:1 ratio, and M$_2$ ml resulted in 1:0 ratios. Storey (1953) hypothesized that both M$_1$ and M$_2$ are completely linked to a lethal gene (1) with a crossing over suppression factor (C), which enforces the heterozygosity on male and hermaphrodite forms. According to Storey's model, no crossing over takes place between I and the other genes of the sex-determining gene block; thus, no lethal-gene-bearing female could possibly be produced. However, approximately 10% of female plants observed in the F$_2$ from F$_1$ plants 6, 8, 9, 13 and 20 suggested that the F$_1$ plants were M$_2$ ml (Table 3), and that the I gene in the SR* showing recombination was not the same as the I gene demonstrated by Storey (1938, 1953). Two genes are proposed to condition the sex expression in the SR* mutant derived from hermaphroditic "Sunrise": one lethal mutant gene (I) tightly linked to m, and another form of the dominant allele.

SR* produces fruit weighing approximately 500 g and tasting like "Sunrise". It can be used to generate all hermaphroditic progenies, and the trait can be transferred to other papaya cultivars. Hybridization of this new gene increases the proportion of hermaphroditic hybrid papaya in the population from 66.7 to 75%. This study shows that the hermaphrodite type could be genetically manipulated and reliably obtained, and would increase the profitability of papaya cultivation.

What is claimed is:

1. A seed of papaya inbred line designated Taiwan Seed Station No. 7 (TSS No. 7), wherein a representative sample of seed of said line has been deposited under ATCC Accession No. PTA.

2. A papaya plant, or a part thereof, produced by growing the seed of claim 1.

3. A papaya plant which is an all hermaphrodite papaya, having all the physiological and morphological characteristics of the papaya plant of claim 2.

4. An inbred papaya plant, or a part thereof, having all the physiological and morphological characteristics of the plant according to claim 2.

5. A pollen produced from the plant of claim 2.

6. A tissue culture of regenerable cells produced from the plant of claim 2.

7. An off-shoot obtained from the plant of claim 2.

8. A cutting obtained from the plant of claim 2.

9. A grafting obtained from the plant of claim 2.

10. A papaya plant regenerated from the tissue culture of claim 6, said plant having all the morphological and physiological characteristics of inbred line TSS No. 7, wherein a representative sample of seed of said line has been deposited under ATCC Accession No. PTA.

11. A method of producing an F1 hybrid papaya seed, comprising crossing the plant of claim 2 with a different papaya plant and harvesting the resultant F1 hybrid papaya seed.

12. A pollen produced from the plant of claim 4.

13. A tissue culture of regenerable cells produced from the plant of claim 4.

14. An off-shoot obtained from the plant of claim 4.

15. A cutting obtained from the plant of claim 4.

16. A grafting obtained from the plant of claim 4.

17. A method of producing an F1 hybrid papaya seed, comprising crossing the plant of claim 4 with a different papaya plant and harvesting the resultant F1 hybrid papaya seed.

* * * * *